(12) United States Patent
Bova et al.

(10) Patent No.: US 6,387,330 B1
(45) Date of Patent: May 14, 2002

(54) METHOD AND APPARATUS FOR STORING AND DISPENSING REAGENTS

(75) Inventors: George Steven Bova, 1000 Fell St., Apt. 510, Baltimore, MD (US) 21231; Stephen B. Leighton, Silver Spring, MD (US)

(73) Assignee: George Steven Bova, Baltimore, MD (US)

( * ) Notice: Subject to any disclaimer, the term of this patent is extended or adjusted under 35 U.S.C. 154(b) by 0 days.

(21) Appl. No.: 09/547,623

(22) Filed: Apr. 12, 2000

(51) Int. Cl.⁷ .............................. B01L 3/02; G01N 1/10; B65B 1/04; B65B 3/04; B67D 5/52
(52) U.S. Cl. ..................... 422/100; 436/180; 73/864; 73/863.32; 73/864.01; 73/864.11; 73/864.13; 73/864.16; 73/864.17; 73/864.31; 141/102; 141/104; 222/135; 222/136
(58) Field of Search .................. 422/100; 436/180; 73/864, 863.32, 864.01, 864.11, 864.13, 864.16, 864.17, 864.31; 141/102, 104; 222/135, 136

(56) References Cited

U.S. PATENT DOCUMENTS

| | | | | |
|---|---|---|---|---|
| 3,650,306 A | * | 3/1972 | Lancaster | |
| 4,158,035 A | * | 6/1979 | Haase et al. | |
| 4,444,062 A | * | 4/1984 | Bennett et al. | |
| 4,779,467 A | * | 10/1988 | Rainin et al. | |
| 5,061,449 A | * | 10/1991 | Torti et al. | |
| 5,306,510 A | * | 4/1994 | Meltzer | |
| 5,360,596 A | * | 11/1994 | Pennatto | |
| 5,456,879 A | * | 10/1995 | Suovaniemi | |
| 5,762,877 A | * | 6/1998 | Brewer | |
| 5,916,524 A | * | 6/1999 | Tisone | |
| 5,927,547 A | * | 7/1999 | Papen et al. | |
| 5,935,859 A | * | 8/1999 | Elliot et al. | |
| 6,063,339 A | * | 5/2000 | Tisone et al. | |
| 6,083,762 A | * | 7/2000 | Papen et al. | |
| 6,105,636 A | * | 8/2000 | Scatizzi et al. | |
| 6,143,252 A | * | 11/2000 | Haxo, Jr. et al. | |
| 6,182,719 B1 | * | 2/2001 | Yahiro | |
| 6,203,759 B1 | * | 3/2001 | Pelc et al. | |
| 6,254,826 B1 | * | 7/2001 | Acosta et al. | |
| 2001/0036425 A1 | * | 11/2001 | Gazeau et al. | |

\* cited by examiner

*Primary Examiner*—Jill Warden
*Assistant Examiner*—Brian R. Gordon
(74) *Attorney, Agent, or Firm*—Pendorf & Cutliff

(57) ABSTRACT

A method and device for storing and dispensing specified subsets from a collection of tens, hundreds or thousands of different reagents to specified locations within microtitre trays or microarray substrates or the like. The reagents of interest are stored in racks of syringe-like dispensers. These dispensers and/or substrates and/or actuators are controllably moved by automated means to a dispensing position where a single action, vibration and weighing system transfers a controlled quantity to a specified location in a microtitre tray or the like. Deficits of the prior art, such as evaporation, cross-contamination, oxidation, waste of reagents and lab-ware, and human operator non-reliability are overcome.

23 Claims, 2 Drawing Sheets

METHOD AND APPARATUS FOR STORING AND DISPENSING REAGENTS

BACKGROUND OF THE INVENTION

1. Field of the Invention

The invention relates to a method and device capable of storing and dispensing specified subsets of materials from large collections (tens, hundreds, or thousands) of different reagents into specified locations within microtitre trays or the like.

2. Description of the Related Art

During the last half of the 20th century, and especially in the 1980's and 1990's, technology has been developed to illuminate the molecular basis of life and disease. Illnesses with homogeneous molecular underpinnings such as sickle cell anemia were the first to be elucidated on a molecular level. More complex diseases, such as cancer, are more difficult to disentangle because their molecular origins involve interaction of multiple defects which may be unique to individual patients.

Researchers working to understand complex diseases or other complex biological issues often start with a general hypothesis, asking a specific molecular question of multiple stored tissue reagent samples such as DNA, RNA, protein, or other materials isolated from diseased or normal tissues. In current practice, these stored samples are stored in liquid form in individual receptacles usually made of plastic, either individually or in groups of 96, 384, or even 1536 wells, for example. The placement of these tissue reagents in fixed positions in storage plates facilitates the use of automated and non-automated multi-headed pipettors to move aliquots of the tissue reagent sample from the storage container to a reaction container.

In current practice, the liquid tissue reagent samples contained in such gridded storage devices are held in place at the bottom of each storage vessel by gravity, and the upper surface of each liquid sample is in contact with air, or in some cases, with pure nitrogen. Ambient air contains 21% oxygen, which over time has a marked, damaging oxidative effect on biological samples. Exposure of each liquid sample to air is inevitable in this current practice because the fill level of each storage receptacle must be kept well below the upper limit of the container to avoid spill-over of the liquid when pipette tips enter the vessel to effect transfer of the liquid to a reaction vessel, causing upward displacement of the liquid within the vessel. Gaseous nitrogen or other less reactive pure gases can be blown into the storage vessel prior to closure, but such systems are not in wide use because of their expense and relative complexity.

When not in use, each gridded or non-gridded liquid reagent storage container must be capped or otherwise sealed, which in current practice usually involves the use of pressure fitted plastic closures, or adhesive films. Each time the pressure fitted closures or adhesive films must be removed to gain access to the stored sample, opposing forces must be applied to the closure land the storage vessel, often leading to vibration or sudden movement which can aerosolize liquid within the storage vessel, increasing the risk of cross-contamination between samples.

In Current practice, transfer of liquid reagent from such a storage device inevitably requires use of a "vector" device, such as a pipette tip, or hollow needle, that enters the sample, removes a volume of liquid and then is moved to a recipient receptacle where a volume of the tissue reagent is dispensed. During subsequent rounds of reagent liquid pickup and dispensing with other samples, new pipette tips must be used, or the needles or pipette tips must be washed to prevent cross-contamination. Use of disposable pipettes is associated with large volumes of unrecyclable plastic waste that must be disposed of, and use of washable needles or pipette tips even under ideal conditions is associated with an irreducible minimum possibility of cross-contamination, which is unacceptable in many research and clinical settings.

For researchers trying to untangle complex biological processes, the current practice of storing liquid reagent samples becomes most troublesome after results are obtained from a first experiment designed to test a general hypothesis. Often this initial experiment will reveal findings in specific subsets of the original tissue samples that require a series of experiments to be performed on only these subsets. To obtain aliquots of the subset of stored reagents needed for these secondary experiments, the researcher must either manually remove the samples needed from the gridded reagent samples, or must have a method of automating this process. Manual removal of liquid samples from such gridded reagents is difficult and error-prone, because it entails identification of small isolated tubes or individual cells within hundreds of cells, careful removal of the cap or adhesive closure for that specific tube or cell, and selective aliquotting using a manual pipettor. Most laboratories, even relatively large ones, find it too expensive to automate this "subset aliquotting", because of the difficulty of addressing individual cells accurately and without risk of contamination to other cells.

In summary, libraries of biological reagents such as cDNA solutions are often stored in collections of passive vessels such as microbitre trays. Such collections typically contain 100's, 1000's or even in excess of 10,000 different reagents. It is necessary to select and transfer specific subsets of these libraries to other vessels or titre trays for subsequent operations or experiments. This is typically done in the present art by pipetting or aspirating and dispensing the required volumes from the storage containers in to the desired recipient locations. This pipetting can be done by hand or by computer controlled robots or laboratory workstations.

Hand pipetting, although involving only inexpensive tools, is obviously prone to human operator error. Only one error in 100 can be very expensive in terms of the invalidity of the results of subsequent experiments. Hand pipetting also shares many of the drawbacks of automated pipetting mentioned below.

Automated pipetting, although avoiding some of the errors of hand pipetting, still involves first aspirating a controlled volume from the storage reservoir (e.g. a microtitre tray) into an intermediate reservoir (the pipette), and then dispensing some or all of that volume into the desired recipient container (e.g. another microtitre tray). This procedure wastes some of the valuable reagent on the walls of the intermediate container, risks cross-contaminating the primary storage volumes, and involves a continuing cost of replacing disposable pipette tips. In addition, this procedure, whether manual or automated, exposes the primary storage volumes to the ambient atmosphere with attendant evaporative losses and contamination including oxidation.

Crude attempts in the prior art to improve the speed of dispensing operations have utilized multiple dispensing heads. However, these devices (manual and automatic) still involve waste of disposable pipette tips and/or cross contamination. Some of these devices employ vibration to create small droplet sizes, but the vibrating unit is at or near the dispensing tip and the plungerl for bulk fluid movement is separated from the dispensing tip by a flexible tube. This results in a cumbersome arrangement and separate plunger actuators and vibrators must be used for each dispensing head. There are no examples in the prior art of more than 4 such heads being used in any such instrument because it was known that the cost would be prohibitive.

U.S. Pat. No. 5,658,802 (Hayes et al.) teaches arrays of electromechanical dispensers to form extremely fine drops of fluid and locate them precisely on substrate surfaces in miniature arrays, wherein a positioning support such as an X-Y table moves the dispensing devices and substrate surfaces relative to each other to locate the drops on the substrates. However, the valving scheme is cumbersome and requires purging each time a switch is made to a different reagent. This wastes time and reagent and is more expensive to build, since a network of valves and tubing must be provided. This valving scheme is required since the electromechanical droplet forming means is not shared by the various tips but the tips are shared by various reagent reservoirs.

U.S. Pat. No. 5,958,342 (Gamble et al.) teaches a particular type of piezo electric dispensing nozzle useful for producing microspots, wherein a pulse jetting device is employed having a capillary of micron dimensions, with a portion of the capillary proximal end of the jetting device circumferentially surrounded by a piezoelectric transducer. The piezoelectric element is bonded tightly to the nozzle and can not be shared between multiple nozzles. There is no mention of an array of devices, only of an array of spots created by this device on a solid substrate.

U.S. Pat. No. 6,001,309 (Gamble et al.) begins with the immediately above described nozzle mechanism, and assembles it into a larger system for making microarrays. A robotic system is used to move the piezoelectric nozzles to and from a filling station where they are refilled with different reagents. Again, the tips are shared by different reservoirs and the piezoelectric elements are dedicated, one integral with each tip.

U.S. Pat. No. 5,981,733 (Gamble et al.) teaches a variation of the above including a reaction chamber with cumbersome valving means, washing means and other subsystems.

U.S. Pat. No. 5,927,547 (Papen et al.) teaches a piezoelectric transducer and a glass capillary for dispensing microvolumes of fluid.

As can be seen from the above, high precision mechanical devices are known, but the basic problems of cross contamination, oxidation, and waste of reagent and dispensing tips have not yet been solved.

SUMMARY OF THE INVENTION

In view of the foregoing disadvantages in known methods of transferring reagents, it is an object of the present invention to build on the technology available in this art, as described above, end to provide an improved method and device for transferring reagents.

These and other objects have been achieved by the present invention which is based on the idea of providing a plurality of reagent-filled syringe-like containers in a rack, each container having a dedicated dispensing tip, for direct dispensing of reagent to micro-titre trays, which are subsequently used in the forming of microarrays. The invention further provides a dispensing means comprising an actuator for displacing reagent from the containers, and preferably also vibration or touch contact means to overcome surface tension and to precisely dispense very fine amounts of reagent. This dispensing means is moveable relative to the rack, such that only one actuator and one vibrator are required, which are brought into operable engagement with the container plunger and the container dispenser tip, respectively, at the time of dispensing reagent. Finally, the invention preferably includes a precision scale for measuring the dispensed amounts of reagent.

One or more such racks can be used in the invention, each one individually inserted into the instrument or returned to cold storage, for example. Alternatively, there may be one such rack dedicated to the device and the entire device may be maintained at a temperature suitable for long-term storage stability of the reagents.

In a first embodiment of the invention, an x-y-positioning system, typically under computer control, can move the rack so that any one of the 10 or more, preferably 100 or more syringe like containers can be at a central dispensing position. An independent x-y-positioning system can move a system of recipient reservoirs, such as a microtitre tray so that any one of the recipient reservoirs is directly under the same dispensing position. Permanently at the dispensing position, preferably directly above the syringe like container from which reagent is to be dispensed, is provided an actuator (e.g. a stepper motor driven lead screw) that can move the plunger of the syringe at the dispensing position. Also permanently at the dispensing position is a means for causing very precise amounts of fluid to be dispensed, and more specifically, to overcome the surface tension of fluids. For example, means may be provided for creating fine droplets using a vibrating device such as a piezoelectric crystal or electromagnetic or mechanical or even fluidic or pneumatic vibrator. The fine droplets permit the dispensed volume to be resolved in very small increments (e.g. 0.05 microliters). The plunger actuation means is capable of both advancing and retracting the plunger. One single plunger actuation means and one single vibrating means are thus shared by all of the syringes in all of the racks. An alternative means for precisely dispensing fine amounts may involve moving the dispensing tip and substrate relative to each other to cause the tip to touch the substrate.

In an alternative embodiment of the invention, a first x-y-positioning system can move the dispensing system while the rack of syringes remains fixed relative to the laboratory. In this embodiment, a second x-y-positioning system can be used to move the microtitre tray as in the first embodiment.

In fact, any two of the three major elements (tray, rack, and dispensing means) may be moved in the x-y plane while the third remains fixed. Thus, the third possibility is for the microtitre tray to remain fixed while the rack of syringes and the shared dispensing means are independently moved.

A weighing scale is provided under the group of recipient reservoirs. This scale continuously monitors the cumulative weight of the collection of recipient reservoirs and thus serves as the control means that can stop the dispensing whenever the desired weight of reagent has been dispensed. Scales are available commercially that have the required full-scale range and fine resolution to weigh a microtitre tray to better than 0.01 mg.

A preprogrammed list of the locations of the reagent in their storage racks, the desired weight of each to be delivered and the desired recipient locations allows an automated controller to move each of the required storage reservoirs into position in turn, to move the corresponding recipient reservoir into position and to dispense a precise amount of reagent. The reagent dispensing cycle is repeated until the list is completed. The rack of stored reagents, typically not fully depleted in one round of dispensing, may now be returned to a suitable storage environment, such as a refrigerated area. Computer control may also keep track of the estimated volume remaining in each of the storage reservoirs and notify the operator if reagent reservoirs need any replenishing.

A cassette or other casing or enclosure may be provided to protect the rack of syringes during storage and transport to and from storage. The atmosphere in this enclosure may be controlled (e.g. dry nitrogen) in order to further protect the contents from oxidation and contamination. This atmosphere may be maintained either by continuous flow or by having a perfectly sealed enclosure that is filled with the controlled atmosphere once before storage.

An alternate embodiment of the collection of syringes comprises plungers without elongated handles, and a single extension handle or plunger shaft attached to the actuator means and shared by all the syringes. This arrangement reduces the height of the rack of syringes when they are full and thus reduces the space required for storage.

A yet further alternate embodiment of the present invention eliminates the vibrating means for causing the droplets that are being dispensed to leave the pipette tips or nozzles at the ends of the syringes. In this embodiment, an additional actuator, preferably placed near the actuator for the syringe plunger, advances the selected syringe as a whole (body plus plunger plus plunger actuator) a small, controlled distance below the other syringes in the cassette of syringes. This motion, possibly combined with appropriate x-y motion of the receiving vessel with respect to the cassette of syringes, causes the tip of the syringe to touch the sidewall or bottom of the receiving vessel. When the tip touches the receiving vessel, any droplets on the end of the syringe will transfer to the receiving vessel due to the surface tension of the droplets and attraction of the receiving vessel. This technique is well-known in the manual art of pipetting and is often called touching-off. It is not known to apply this to direct syringe storage/dispense automated devices such as the present invention.

This embodiment has the advantage of simplicity and lower cost by eliminating the vibrating means. There is a potential disadvantage of cross-contamination of the dispensing syringe and tip by any foreign matter in the receiving vessel. Thus for some applications, this would not be the preferred embodiment, but for many applications the receiving vessels are known to be perfectly clean and sterile and not to contain any foreign matter, and in such circumstances this simpler embodiment would be preferred.

The advance of the selected syringe below the others may also be used to advantage with the vibrating embodiment, in order to place the tip of the active syringe within or at least closer to the receiving vessel prior to dispensing.

It is emphasized that in this and all other embodiments described in this application, only the actuating means is shared by the different storage/dispense containers. Each dispensing container has its own tip or dispensing nozzle. This aspect clearly distinguishes the present invention from prior art such as U.S. Pat. No. 5,658,802, which use cumbersome valving arrangements to share tips among numerous storage reservoirs. These arrangements require complicated purging techniques which waste reagents and time.

It should also be noted that all embodiments of the present invention could be applied to printing micro arrays of reagents on planar solid substrates, as described in U.S. Pat. Nos. 5,658,802, 5,958,342 and others, besides dispensing to discrete receiving vessels as primarily described.

Thus, precise dispensing is enabled without any of the disadvantages of the prior art. Cross-contamination, evaporative loss or oxidation of unused reagent is markedly reduced or eliminated. New pipetter tips are not required for each dispensing operation. Human errors and fatigue are avoided.

BRIEF DESCRIPTION OF THE DRAWINGS

For a fuller understanding of the nature and objects of the present invention reference should be made to the following detailed description in conjunction with the accompanying drawings in which.

DETAILED DESCRIPTION OF THE INVENTION

Figure 1:
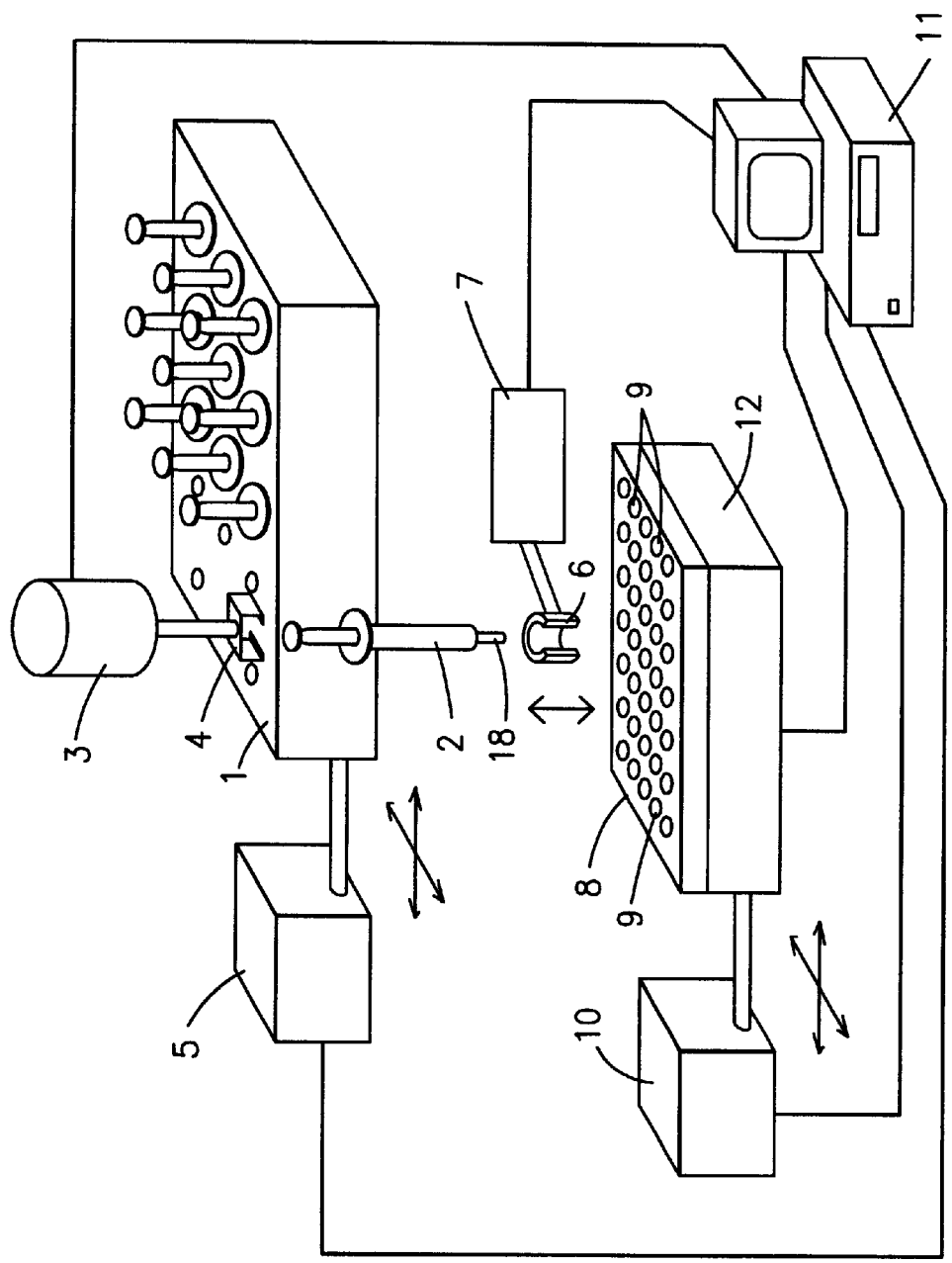
FIG. 1 is an isometric schematic and block diagram of the first embodiment of the invention.

With reference to FIG. 1, 1 is a rack containing tens, hundreds or even thousands or more syringe-like containers. 2 is a single one of these containers, and is removable and replaceable in the rack or refillable while still in place. The other hundreds of identical containers are not shown in their entirety, to lend clarity to the drawing. The body of each syringe is clamped in the rack by clamping means not shown. The entire rack can be positioned in a horizontal plane by x-y-actuator means 5. Of course, a cylindrical coordinate system or a conveyor-belt system could be used as well, but an x-y-positioning system is preferred. The syringe that is desired to be utilized is positioned under plunger actuator 3 and connected with clamping means 4 of the actuator. Simultaneously, vibration means 7 is coupled with coupling means 6 which rises to meet and mate with the dispensing tip of syringe 2. Of course, in view of the large number and close proximity of the dispenser tips, the shape and movement path of the coupling means 6 is designed to avoid other dispensing tips. Recipient reservoir collection 8 contains a number of recipient wells 9 and rests on weighing scale 12. Any one of the reservoirs can be moved under the dispensing syringe by x-y-actuator 10. The weight of the reservoir collection is monitored by control means 11 which also commands the two x-y- actuators, the plunger actuator and the vibration means.

Since the plunger tops may be at varying elevations after the rack has been used for a while, or after racks have been exchanged, the plunger actuator may be provided with a contact sensor for recognizing contact with the plunger tops, or the computer may be provided with memory for recording the last known position of the plunger tops.

As an alternative to the clamping means 4 the plunger may have any well known coupling means, including threading, slotting a mating surface for a vacuum fitting, etc.

The coupling means 6 may be a set of jaws, at least one of which is moveable towards the other, for releasably clamping onto the dispenser tip 16 for and forming solid contact transmission of vibrations from the vibration means 7. Since the vibrator moves in a reciprocating fashion, the coupling means should provide good contact at least on the side of the dispenser tip facing the vibrator and the side of the dispenser tip opposite to the vibrator. Alternatively, the coupling means may be in the form of a non-clamping fork or V which receives and nestles the dispensing tip between the prongs of the fork or arms of the V at the time of dispensing.

Figure 2:
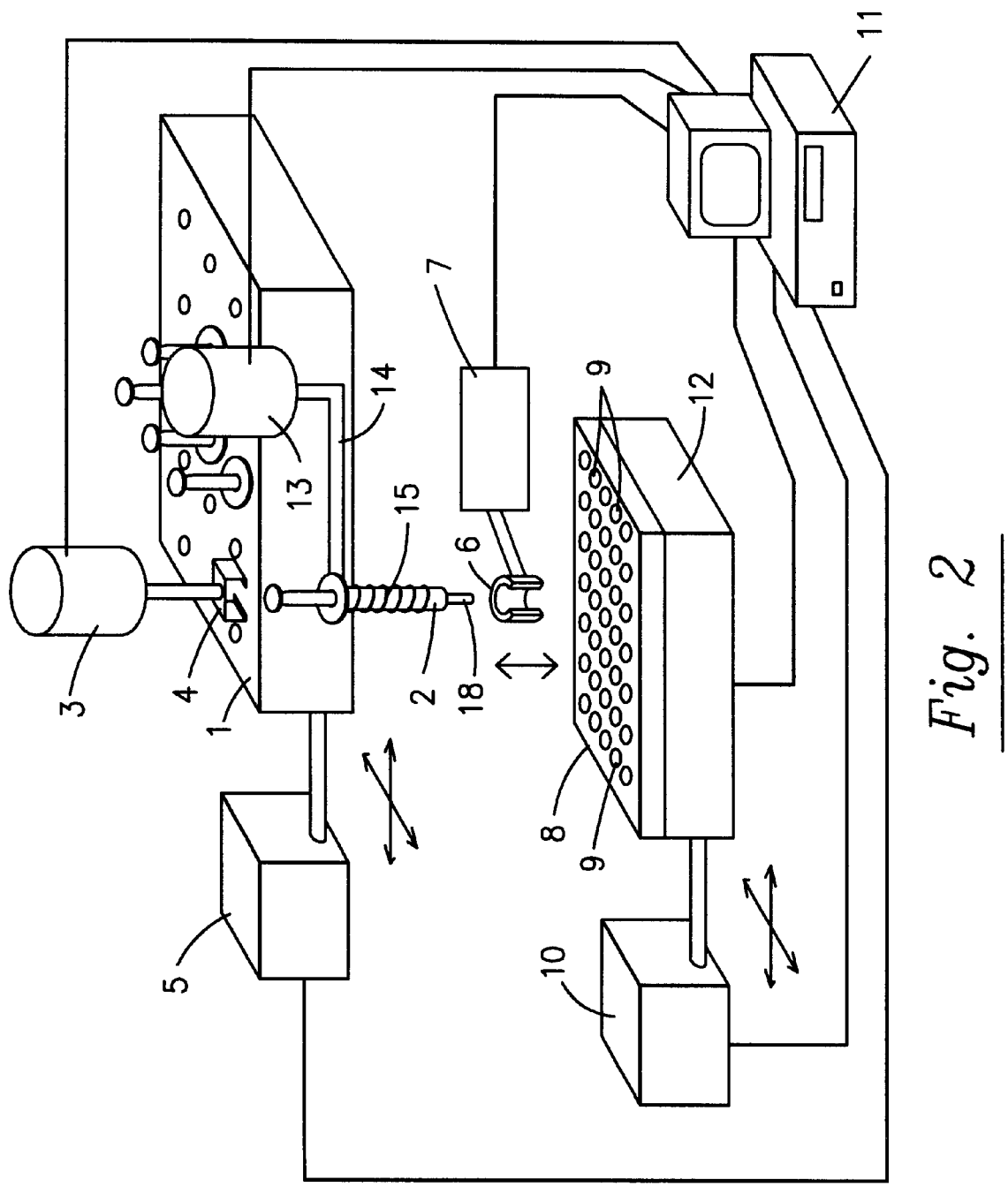
FIG. 2 is an enlarged partial view corresponding to FIG. 1, but showing a second embodiment of the invention wherein vibration dispensing is replaced by contact dispensing.

FIG. 2 shows the second embodiment of the invention corresponding in large part with the first embodiment, wherein like elements are given the same reference numbers, and wherein actuator 13 (shown highly schematically) via arm 14 can push syringe/reservoir 2 substantially vertically (z-axis) downward against restoring spring 15. Contact may be monitored and controlled via feedback means, or may simply involve precise pre-alignment of all tips to a start plane, from which start plane all movement to the surface of the substrate is the same, fixed distance.

Depending upon the construction materials selected, it is even possible in accordance with a third embodiment of the invention to introduce vibration energy from the plunger side of the dispensing container, preferably directly from the actuator, such that vibrations are transmitted through the incompressible reagent medium and to the dispensing tip, rather than providing a separate complex means which must be positioned and securely connected to the dispensing tip for inputting vibratory energy at the dispensing tip side of the reservoir. While such a variation input is less efficient in the sense of requiring a greater energy input and requiring comparatively non-deformable dispensing containers (e.g., glass or rigid plastic syringes, and with stiffer plastic or rubber replacing soft rubber plungers), this disadvantage may be offset by the savings attributable to not having to provide a vibrator capable of being moved into position, accessing the selected dispenser tip, grasping the dispenser tip, and inputting vibrations to the dispenser tip. Such an embodiment would appear similar to the embodiments shown in FIGS. 1 and 2, except that a vibrator would be incorporated into actuator 3, and vibrator 7 and grasping means 6 would be dispensed with. In this an embodiment the dispenser end of the reservoir is preferably conical or funnel shaped, to focus or amplify vibration energy in the area of the tip.

A yet further alternative to the introduction of vibration at the dispenser tip side of the reservoir and the introduction of vibration at the plunger side of the reservoir envisions the introduction of vibration energy at the sidewall of the reservoir. In this case the reservoir is preferably made of a resilient plastic transmissive to vibrations, but may also be more solid, e.g., glass. The sidewall of the reservoir may be cylindrical or may be flattened. The vibrator may be coupled to the actuator 13, or may be moved independently of the actuator.

It may be desirable or even necessary to isolate the scale mechanism and recipient reservoirs from vibration, whether such vibration comes from the external environment or from the dispensing or x-y mechanisms themselves. This isolation can be done by any number of well-known ways, such as vibration isolation pads. The control computer may also be programmed to appropriately filter the weight signal to eliminate some spurious readings from vibrations, and the weighing would preferably not be done while any of the x-y mechanisms are running, anyway.

Another advantage of the present invention is that the computer or control means may be programmed to fill the storage containers without requiring the addition of any additional physical components. Supply containers of new reagents that are desired to be used to refill any of the storage reservoirs in the rack(s) of the present invention may be placed in the area of the recipient reservoirs in their stead, and the plunger actuator may be used to retract the plunger and draw new material from the supply container(s) into one or more storage reservoirs, one at a time. The supply containers may be microtitre trays. Just as the reservoir in the rack may be advanced below the other reservoirs for dispensing, so may it also be advanced to reach into a supply container.

An alternate embodiment of the invention uses a timed pneumatic (eg air) pulse of regulated pressure applied to the plunger of the active syringe instead of a direct mechanical force such as a lead screw. The plunger piston and seal would still be present to separate the reagent from the pneumatic media (eg air). This embodiment, in some applications, may have advantages of simplicity and finer control. The single shared pneumatic source may be coupled to whichever syringe is active by any number of quick connect means, such as deformable or inflatable seals or o-ring or face seals with corresponding means of holding or clamping the sea. Alternatively, a variety of valve manifolds or the pneumatic vale equivalent of cross-point switches could be used to direct the pneumatic pulse to the syringe of interest, avoiding the necessity of clamping and sealing repeatedly to the various syringes, although such arrangements would share some of the cumbersome qualities of the prior art. Commercially available devices include Model 1500XL produced by EFD, Inc. of E. Providence, R.I.

It may be necessary/desirable to use an enclosure not only to keep the entire instrument clean and safe, but also to prevent ambient air currents from exerting convective forces on the reservoir array and weighing scale, which would interfere with the accuracy of the measurement of the amounts dispensed. Further, it may e desirable to provide a means of dissipating any static electric charges present on the reservoir/scale system, as these could also interfere with the weighting. These charges can be dissipated with controlled high humidity or with ion sources, both well known and commercially available for dissipating static electricity.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Now that the invention has been described,
What is claimed is:
1. A device for storing collections of different reagents and dispensing specified subsets of reagents to specified locations on a substrate, said device comprising:

two or more dispensing containers assembled into a rack, each of said dispensers including a reservoir containing a reagent, a dispenser tip in fluid communication with said reservoir, and a plunger in communication with said reservoir, an actuator adapted for releasable operable engagement with said plunger;

positioning means for positioning a receiving surface;

first repositioning means for repositioning at least one of said rack, actuator, and receiving surface; and second repositioning means repositioning at least another of said rack, actuator, and receiving surface;

wherein reagent can be dispensed from said dispenser tip at a desired location relative to said receiving surface by positioning one of said reservoirs relative to said surface, bringing said actuator into operable engagement with the plunger associated with said reservoir, and activating said plunger.

2. A device as in claim 1, further including means for vibrating said dispensing tip.

3. A device as in claim 2, wherein said means for vibrating said dispensing tip is releasably in vibrating contact with said dispenser tip.

4. A device as in claim 2, wherein said means for vibrating said dispensing tip is releasably in vibrating contact with said plunger.

5. A device as in claim 2, wherein said means for vibrating said dispensing tip is releasably in vibrating contact with at least one side wall of said reservoir.

6. A device as in claim 2, wherein said means for vibrating includes a vibrator selected from the group consisting of piezoelectric crystals, electromagnetic vibrators, mechanical vibrators, hydraulic vibrators, and pneumatic vibrators.

7. A device as in claim 1, further including means for moving said dispensing container towards said substrate and contacting said dispenser tip to said substrate during said dispensing.

8. A device as in claim 1, wherein said first and second positioning means are x-y positioning means.

9. A device as in claim 8, further including computer control means for controlling said x-y positioning means.

10. A device as in claim 9, wherein said computer control means directs the positioning of the actuator means relative to the rack, the engagement of actuator means with the desired plunger, and the activation of the plunger for dispensing reagent.

11. A device as in claim 8, further including a scale for weighing the amount of reagent deposited on said substrate and including communication means for communicating said weighed amount to said computer.

12. A device as in claim 1, further including a scale for weighing the amount of reagent deposited on said substrate.

13. A device as in claim 1, wherein said rack is designed to be removeable and replaceable.

14. A device as in claim 13, comprising two or more racks.

15. A device as in claim 1, wherein said reagent dispensers are arranged along an x-y grid.

16. A device as in claim 1, wherein said first repositioning means repositions said receiving surface, and wherein said second repositioning means repositions said rack.

17. A device as in claim 1, wherein each of said plungers is connected to a plunger shaft, and wherein said actuator includes grasping means for grasping a plunger shaft.

18. A device as in claim 1, wherein said substrate is a microarray.

19. A device as in claim 1, wherein said substrate is a microtitre tray.

20. A device as in claim 1, wherein ten or more dispensing containers assembled into said rack.

21. A device as in claim 1, wherein twenty or more dispensing containers assembled into said rack.

22. A device as in claim 1, wherein one hundred or more dispensing containers assembled into said rack.

23. A device as in claim 1, wherein said device includes a computer programmed to monitor the fill level of said dispenser containers, and to add reagent to dispenser containers when the fill level drops below a programmed threshold.

* * * * *